United States Patent [19]

Taylor

[11] Patent Number: 5,736,164
[45] Date of Patent: Apr. 7, 1998

[54] FUNGICIDAL COMPOSITIONS FOR PLANTS CONTAINING PHOSPHONATE AND PHOSPHATE SALTS, AND DERIVATIVES THEREOF

[76] Inventor: John B. Taylor, 1420 Lemon St., DeLan, Fla. 32720-4599

[21] Appl. No.: 705,594

[22] Filed: Aug. 30, 1996

[51] Int. Cl.$^6$ .................................................. A01N 59/26
[52] U.S. Cl. ........................................ 424/601; 424/605
[58] Field of Search .......................... 424/601, 605

[56] References Cited

U.S. PATENT DOCUMENTS

| | | | |
|---|---|---|---|
| 1,935,599 | 11/1933 | Rippey | 99/1 |
| 3,798,020 | 3/1974 | Parham, Jr. et al. | 71/1 |
| 4,075,324 | 2/1978 | Thizy et al. | 424/128 |
| 4,119,724 | 10/1978 | Thizy et al. | 424/45 |
| 4,139,616 | 2/1979 | Ducret et al. | 424/222 |
| 4,542,023 | 9/1985 | Lacroix et al. | 514/126 |
| 4,698,334 | 10/1987 | Horriere et al. | 514/141 |
| 4,755,614 | 7/1988 | Corbet | 558/134 |
| 4,780,458 | 10/1988 | Hodakowski et al. | 514/112 |
| 4,806,445 | 2/1989 | Horriere et al. | 514/141 |
| 4,849,219 | 7/1989 | Staub | 424/605 |
| 4,935,410 | 6/1990 | Barlet | 514/75 |
| 5,070,083 | 12/1991 | Barlet | 514/144 |
| 5,124,344 | 6/1992 | Greiner et al. | 514/383 |
| 5,133,891 | 7/1992 | Barr et al. | 252/20 |
| 5,169,646 | 12/1992 | Horriere et al. | 414/632 |
| 5,206,228 | 4/1993 | Collins | 514/141 |
| 5,246,953 | 9/1993 | Greiner et al. | 514/383 |
| 5,290,791 | 3/1994 | Greiner et al. | 514/383 |
| 5,342,835 | 8/1994 | Pepin et al. | 514/227.5 |
| 5,358,958 | 10/1994 | Greiner et al. | 514/383 |
| 5,395,418 | 3/1995 | Vetanovetz et al. | 71/29 |
| 5,514,200 | 5/1996 | Lovatt | 71/11 |

OTHER PUBLICATIONS

P. Widdowson and H.P. Rothbaum, The Use of Red Phosphorus as a Fertilizer, Sep. 1964, pp. 427–445 New Zealand Journal of Science.

George Malacinski and Walter A. Konetzka, Bacterial Oxidation of Orthophosphite, Feb., 1966, pp. 578–582 Journal of Bacteriology.

Fred Adams and John P. Conrad, Transition of Phosphite to phosphate in soils, Jul. 1952, pp. 361–371.

D.I. Guest and G. Bompe Ix, The Complex Modeof Action of Phosphontates, 1990, pp. 113–115, Australasian Plant Pathology, vol. 19, No. 4.

B.R. Grant, R.H. Dunstan, J.M. Griffth, J.O. Niere and R.H. Smillie, The Mechanism of Phosphonic (phosphorouse acid in Phytophthora, 1990, pp. 115–121, The Australasian Plant Pathology, vol. 19, No. 4.

R.H. Dunhill, The Manufacture and Properties of Phosphonic (Phosphorous) Acid, 1990, pp. 138–139, Australasian Plant Pathology, vol. 19, No. 4.

*Primary Examiner*—Allen J. Robinson
*Attorney, Agent, or Firm*—Lathrop & Gage LC

[57] ABSTRACT

A fungicidal composition for plants containing phosphonate and phosphate salts, and derivatives thereof is disclosed. The composition provides a single product which may be employed to control parasitic fungi in plants through mitigation of pathological acerbation of certain fungi.

8 Claims, No Drawings

FUNGICIDAL COMPOSITIONS FOR PLANTS CONTAINING PHOSPHONATE AND PHOSPHATE SALTS, AND DERIVATIVES THEREOF

BACKGROUND OF THE INVENTION

The present invention is broadly concerned with fungicidal compositions, and methods of use, which provide improved efficacy in controlling parasitic fungi in plants. More particularly, the compositions and methods of use of the invention include fungicidally effective amounts of both phosphate, preferably in the form of either mono or dipotassium phosphate ($KH_2PO_4$, $K_2HPO_4$) and phosphonate, preferably in the form of either mono or dipotassium phosphonate ($KH_2PO_3$, $K_2HPO_3$), in aqueous solution.

Phosphorus is an essential major element in plant nutrition because it governs the energy producing reactions, including those that are oxidative, and photophosphorylative and the production of adenosine diphosphate (ADP) and adenosine triphosphate (ATP). Energy-rich phosphate bonds of ADP and ATP provide the energy for many of the physiological reactions that occur in plants.

The element phosphorous appears in two general forms that concern the present invention—phosphonate and phosphate. The term "phosphonate," sometimes also referred to as "phosphite," means the salts (organic or inorganic) of either phosphonic acid or phosphorous acid. Phosphonic and phosphorous acids have the formula $H_3PO_3$ and a molecular weight of 82.00. Their structures from the International Union of Pure and Applied Chemistry are shown below:

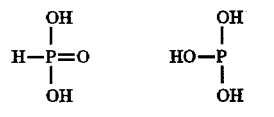

Phosphonic Acid  Phosphorous Acid
CA:13598-36-2    CA:10294-56-1

The term "phosphate" means the salts (organic or inorganic) of phosphoric acid having the formula $H_3PO_4$, molecular weight of 98, and has the following structure:

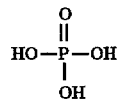

Phosphoric Acid
CA:7664-38-2

In the past, various phosphonate compounds have been proposed as useful in fungicidal and fertilizer compositions for application to plants. See, e.g. U.S. Pat. Nos. 4,075,324 and 4,119,724 to Thizy, describing phosphorous acid, its inorganic and organic salts, as a plant fungicide; U.S. Pat. No. 4,139,616 to Dueret, describing fungicidal compositions based on phosphorous acid esters and salts thereof; U.S. Pat. No. 4,542,023 to Lacroix et al., describing organophosphorous derivatives as possessing systemic and contact fungistatic and fungicidal activity; U.S. Pat. Nos. 4,698,334 and 4,806,445 and 5,169,646 to Horriere et al., describing fungicidal compositions based on alkyl phosphonates; U.S. Pat. Nos. 4,935,410 and 5,070,083 to Barlet, describing fungicidal aluminum tris-alkyl-phosphonate compositions; and U.S. Pat. No. 5,514,200 to Lovatt, describing formulations of phosphorous-containing acid fertilizer for plants. (The teachings of the proceeding U.S. patents are hereby incorporated by reference.) The above references disclose phosphonate compositions have been found to be effective for protecting plants, and particularly grape vines, citrus and fruit trees and tropical plants, against fungal attack.

Once assimilated, phosphonates have been shown to enhance the phytoimmune system. The phosphonate induced stimulation of the phytoimmune system is triggered by the induction of ethylene production, followed by a rapid accumulation of phytoalexins at the site of infection. Phosphonates have also been shown to have detrimental effect on the growth of Phycomycetes. See, Pegg, K. G. and deBoer, R. F., "Proceedings of the Phosphonic (Phosphorous) Acid Work Shop," *Australiasian Plant Pathology*, Vol. 19 (4) 1990.

In accordance with this development of the present invention, however, it has recently been discovered that phosphonates exacerbate the non-target Ascomycete fungi, producing an eiphytotic outbreak of much greater magnitude than the infections occurring without phosphonate treatment. This phenomenon is known as pathological acerbation.

In the past, phosphates were not viewed as a solution to pathological acerbation of Ascomycete fungal infections. This is because phosphates are viewed primarily as a fertilizer with only limited, or even detrimental, fungical properties. For example, U.S. Pat. No. 5,514,200 teaches that phosphate fertilizers inhibit beneficial symbiosis between plant roots and mycorrhizal fungi, and further promote bacterial and fungical growth in the rhizosphere, including the growth of pathogenic fungi and other small soil-borne organisms. (Col. 2, lines 18–28). Phosphates have also been considered to be a competitive inhibitor for phosphonate assimilation, thus inhibiting the ability of phosphonates to protect against fungus attack. See, Pegg, K. G. and deBoer, R. F., "Proceedings of the Phosphonic (Phosphorous) Acid Work Shop," *Australiasian Plant Pathology*, Vol. 19 (4), pp. 117 and 144, 1990. Yet further, phosphonates and phosphates were believed to be "biological strangers," with the presence of phosphonates or its esters, exerting little or no influence on enzyme reactions involving phosphates. Robertson, H. E. and Boyer, P. D., "The Biological Inactivity of Glucose 6—phosphonate, Inorganic Phosphites and Other Phosphites," *Archives of Biochemistry and Biophysics*, 62 pp. 380–395 (1956).

Accordingly, the requirements for a successful phosphonate-based fungicide depend on the elimination of the phosphonate-induced pathological ascerbation of Ascomycete fungical infections.

SUMMARY OF THE INVENTION

The present invention addresses the problems outlined above, and provides an improved anti-fungicidal composition for plants that contains, as active ingredients, fungicidally effective amounts of both phosphonates and phosphates. According to the present invention, it has been discovered that the application to a plant of the inventive phosphonate/phosphate composition substantially eliminates pathological acerbation of Ascomycete fungi, while at the same time, provides a means to control Phycomycetes and Ascomycetes with a single product.

Thus, an object of present invention is to provide a fungicidal composition for protection for plants against fungal infection, especially Phycomycetes and Ascomycetes.

Another object of the invention is to provide such anti-fungal protection with a single product that upon application does not cause pathological acerbation of Ascomycetes infections.

A further object of the invention is to provide a method of treating plants and to provide anti-fungical protection in plants against attack by Phycomycete and Ascomycete fungi.

A yet further object of the invention is to provide an anti-fungal composition for treating plants that is environmentally safe, inexpensive to use and has low mammalian toxicity.

These and other objects of the invention are attained by the invention disclosed below. According to the invention, anti-fungicidal compositions for the protection of plants, especially citrus and fruit trees and vines against fungus attack, preferably contain as an active material a fungicidally effective amount of at least a first salt formula selected from the group consisting of $KH_2PO_3$, $K_2HPO_3$,l and $K_3PO_3$, and at least a second salt selected from the group consisting of $KH_2PO_4$, $K_2HPO_4$ and $K_3PO_4$, in a mixture with an agriculturally acceptable carrier.

The composition preferably comprises an aqueous solution wherein each salt is present in solution from about 20 millimole to about 5% vol./vol..

According to another aspect of the invention, the amount of the first salt is one part by weight and the amount of the second salt is between 0.001 and 1,000 parts by weight.

Phosphonate salts useful in the practice of the invention also include those organic and inorganic salts taught by U.S. Pat. Nos. 4,075,324 and 4,119,724 to Thizy et al., (see, e.g., col. 1, ln. 51–69 through col. 2, ln. 1–4).

A DETAILED DESCRIPTION OF THE PREFERRED EMBODIMENT

The following examples set for preferred concentrations and techniques for formulation thereof, as well as methods of application and use and test results demonstrating the efficacy of the inventive concentration in protecting plants against attack by Ascomycete and Phycomycete fungi. It is to be understood, however, that these Examples are presented by way of illustration only and nothing therein shall be taken as a limitation upon the overall scope of the invention. The specific components tested in the Examples were prepared and applied as follows.

Method of Preparation

A. Potassium Phosphonate ($KH_2PO_3$) Aqueous Solution. $H_3PO_3$ is produced by the hydrolysis of phosphorus trichloride according to the reaction: $PCl_3 + 3H_2O > H_3PO_3 + 3HCl$. The HCl is removed by stripping under reduced pressure and the phosphonic acid ($H_3PO_3$) is sold as a 70% acid solution.

The phosphonic acid is then neutralized in aqueous solution by potassium hydroxide according to the reaction: $H_3PO_3 + KOH > KH_2PO_3 + H_2O$ to about pH 6.5 and to produce a 0-22-20 liquid weighing 11.15 lbs./gal. This solution is commercially available and is sold under the trademark "Phos-Might" by Foliar Nutrients, Inc., Cairo, Ga. 31728.

B. Potassium Phosphate ($K_2HPO_4$) Aqueous Solution. Mono potassium phosphate (0-51.5-34) is reacted with 45% potassium hydroxide in aqueous solution to produce dipotassium phosphate by the following reaction: This solution is commercially available and is sold under trademark "K-Phos" by Foliar Nutrients, Inc., Cairo, Ga. 31724

$KH_2PO_4 + KOH > K_2HPO_4 + H_2O$ with a product density of 1.394 at 20° C. and a solution pH of 7.6 producing a 0-18-20 analysis.

C. $KH_2PO_3/K_2HPO_4$ Solution. Varying amounts of each compound ($K_2HPO_3$; $KH_2PO_3$; $K_2HPO_4$; or $KH_2PO_4$) in aqueous solution are combined at rates ranging from 20 millimole to 5% vol./vol., depending on crop host and the pathogen complex and level of infection.

Method of Application

The preferable method of application is foliar, either by ground or aerial equipment, but is not limited to that method alone. Injection or soil applications, for example, could also be efficacious depending on specific crops and pathogens.

The inventive compositions have utility on fruit crops, agronomic crops, ornamentals, trees, grasses, vegetables, grains, and floricultural crops, as well as, some aquatic crops including water cress.

The fungicidal properties of the compounds according to the invention are various, but are particularly interesting in the case described in the following examples:

Examples 1–5 exemplify a portion of these applications. In Examples 1–4, fungicidal treatments were applied to ornamentals, citrus and vegetables. In each of Examples 1–4, treatments were applied as a one gallon solution by a back pack sprayer, maintained at about 60 psi, in sufficient quantities of water to achieve thorough coverage.

All treatments were applied to the appropriate number of experimental units assigned in a randomized complete block (RCB) design replicated four times. Example #5 was a pre-harvest fungicidal spray evaluation on "Nova" tangelos.

As used in the examples, "percent infection" means percent of leaves that exhibit fungus lesions. "Phytotoxicity" means number crop injury to leaves that fell off the plant following the application of the solution.

The Ascomycete fungi were the subjects of testing in Examples 1 through 5 and are all members of the Ascomycete family.

EXAMPLE NO. 1

Dogwood\Powdery Mildew Fungicide Trial Trail Ridge Nursery, Keystone Hts., Fla.

The compounds according to the invention are studied for the effect on the powdery mildew (*Oidium Spp.*), which is responsible for foliar infections in dogwood.

Potassium phosphonate and potassium phosphate solutions were applied in compositions as set forth in Table 1 below. An average of 5 six-inch pots per experimental unit with 4 repetitions in a randomized complete block ("RCB") design were considered. The solutions were applied to Dogwood (*Cornis Florida Var. "Weaver"*). The application of the compositions were made in Apr. 25, 1996, May 8, 1996, and May 23, 1996. The effects of the various compositions were rated on May 30, 1996.

Table 1 shows that when a potassium phosphonate solution (containing no appreciable amount of phosphate) is applied to dogwood, pathological acerbation of the Ascomycete fungus occurs in 100 percent of the dogwood leaves, in contrast to the control, which exhibited only 30 percent infection. The inventive composition that combine potassium phosphate and potassium phosphonate showed a complete elimination of the pathological acerbation phenomenon, and in fact, dropped the amount of infection by about 20 percent.

TABLE 1

| TREATMENT | RATE/100 gal. | * % INFECTION | PHOTO-TOXICITY |
|---|---|---|---|
| 1) POTASSIUM PHOSPHONATE SOLUTION | 1% | 100 | 0 |
| 2) POTASSIUM PHOSPHATE SOLUTION | 1% | 0 | 0 |
| 3) POTASSIUM PHOSPHONATE SOLUTION + POTASSIUM PHOSPHATE SOLUTION | 1% + 1% | 10 | 0 |
| 4) POTASSIUM PHOSPHATE SOLUTION | 2% | 0 | 0 |
| 5) CONTROL | — | 30 | 0 |

EXAMPLE NO. 2

Shumard Oak/Powdery Mildew Fungicide Trial
Trail Ridge Nursery, Keystone Hts., Fla.

In Example No. 2, the inventive compositions were tested for effectiveness against the powdery mildew (*Phyllactinia corylea*) that infects shumard oak (*Quercus shumardii*). In Example No. 2, an average of ten 3-gallon plots per experimental unit with 4 repetitions in a randomized complete block design were examined.

When only potassium phosphonate solution was applied, the percentage of infection increased to 40 percent, compared to a 20 percent infection in the control, indicating a pathological acerbation of the Ascomycete fungi. When the inventive composition including potassium phosphonate and potassium phosphate was applied, the infection was completely eliminated.

TABLE 2

| TREATMENT | RATE/100 gal. | * % INFECTION | PHOTO-TOXICITY |
|---|---|---|---|
| 1) POTASSIUM PHOSPHONATE SOLUTION | 1% | 40 | 0 |
| 2) POTASSIUM PHOSPHATE SOLUTION | 1% | 0 | 0 |
| 3) POTASSIUM PHOSPHONATE SOLUTION + POTASSIUM PHOSPHATE SOLUTION | 1% + 1% | 0 | 0 |
| 4) POTASSIUM PHOSPHATE SOLUTION | 2% | 0 | 0 |

EXAMPLE NO. 3

Citrus Alternaria Fungicide Trial Kerr Center, Vero Beach, Fla.

In Example No. 3, the inventive composition was tested for effectiveness in citrus trees (*Alternaria citri*) that were infected with the fungi.

As used in Table No. 3 below, "% Y.L.D." means percent young leaf drop, and "% Y.F.D." means percent young fruit drop. % Y.L.D. and % Y.F.D. were determined by examining 4 terminals/tree with 4 repetitions in a randomized complete block design. The date on which the compositions were applied were Mar. 21, 1996. The compositions were rated on Apr. 2, 1996. When only potassium phosphonate solutions were applied, % Y.L.D. and % Y.F.D. increased from 6.2 and 1.5 to 23.9 and 37.9, respectively, indicating pathological acerbation of the Ascomycete fungi. Application of the inventive composition not only eliminated the acerbation, but showed an improvement in Y.L.D. and Y.F.D.

TABLE 3

| TREATMENT | RATE/100 gal. | % Y.L.D. | % Y.F.D. | PHOTO-TOXICITY |
|---|---|---|---|---|
| 1) POTASSIUM PHOSPHATE SOLUTION | 0.5% | 5.2 | 3.8 | 0 |
| 2) POTASSIUM PHOSPHATE SOLUTION | 1% | 2.5 | 2.5 | 0 |
| 3) POTASSIUM PHOSPHATE SOLUTION | 2% | 1.5 | 1.0 | 0 |
| 4) POTASSIUM PHOSPHONATE SOLUTION | 1% | 23.9 | 37.5 | 0 |
| 5) POTASSIUM PHOSPHATE SOLUTION + POTASSIUM PHOSPHONATE SOLUTION | 0.5% + 0.5% | 2.2 | 3.7 | 0 |
| 6) CONTROL | — | 6.2 | 1.5 | 0 |

EXAMPLE NO. 4

Carrot/Alternaria Fungicide Trial

In Example No. 4, carrot plots were inoculated with *Alternaria dauci* fungi. The plot sizes were single rows×25 feet×4 repetitions in a RCB design. The dates that compositions were applied were Feb. 2, 9, 15, 22, and Mar. 8, 14, 22, and 28, 1996. The fungi infections were rated on Apr. 5 and Apr. 23, 1996. The second rating was 25 days after the last fungicide application. The test took place at Sanford, Fla.

Application of the inventive solutions including potassium phosphonate and potassium phosphate improved the extent of infection from that otherwise occurring in the control carrots. Although the solution making use of only potassium phosphonate caused a slight improvement from the infection occurring in the control, it was substantially less than that associated with the inventive composition.

Also shown in Example No. 4 is a comparison of the effectiveness of the inventive composition to other fungicides, including Cu-Alexin and Fe-Alexin. This test demonstrates that the inventive composition is as effective as other well known fungicides, but without being as environmentally toxic.

TABLE 4

| TREATMENT | RATE/100 GAL. | AVG % INFECTION | |
|---|---|---|---|
| | | 4/5/96 | 4/23/96 |
| 1) POTASSIUM PHOSPHATE | 1 % | 6.9 | 8.2 |
| 2) POTASSIUM PHOSPHONATE SOLUTION | 1% | 18.7 | 28.8 |
| 3) POTASSIUM PHOSPHATE SOLUTION + POTASSIUM PHOSPHONATE SOLUTION | 0.5% + 0.5% | 8.9 | 10.7 |
| 4) Cu-ALEXIN | 0.2 lb ai | 8.8 | 11.6 |
| 5) Fe-ALEXIN | 0.2 lb ai | 12.7 | 12.9 |
| 6) CONTROL | — | 23.0 | 34.8 |

EXAMPLE NO. 5

Citrus Preharvest Spray Trials Kerr Center, Vero Beach, Fla.

In Example No. 5, twenty-two fruits, each from five nova tangelo trees, were randomly selected and marked. The fruits were scuffed with an emery board and then sprayed with the compositions set forth below in Table 5, with five treatments on the same day. Seven days later, the fruit was picked and stored for two weeks in sealed white plastic bags, then examined for penicillium mold.

The degree of infection was rated using following scores: 0=no infection, 1=light infection (less than 30% coverage), 2=severe infection (100% coverage). The degree of infection is the mean of scores from 22 fruit.

TABLE 5

| TREATMENT | RATE | DEGREE OF INFECTION | # ROTTEN FRUIT | PHOTO-TOXICITY |
|---|---|---|---|---|
| 1) POTASSIUM PHOSPHONATE SOLUTION | 1% | 1 | 9 | 0 |
| 2) POTASSIUM PHOSPHONATE SOLUTION | 2% | 0.91 | 12 | 0 |
| 3) POTASSIUM PHOSPHATE SOLUTION | 1% | 0 | 0 | 0 |
| 4) POTASSIUM PHOSPHATE SOLUTION + POTASSIUM PHOSPHONATE SOLUTION | 0.5% + 0.5% | 0.27 | 3 | 0 |
| 5) CONTROL | — | 1.41 | 12 | 0 |

The above Examples demonstrate that the inventive composition are useful in protecting plants against attack by both Phycomycete and Ascomycete with the application of one solution.

It will also be appreciated that compositions for controlling Phycomycete and Ascomycete fungi diseases in plants may also contain phosphate and phosphonate compounds comprising a fungicidally effective amount of at least a first salt having the following formula:

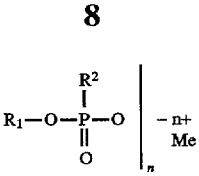

And a second salt having the following formula:

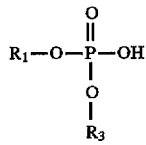

Where $R_1$ is selected from group consisting of H, K, an alkyl radical containing from 1 to 4 carbon atoms, halogen-substituted alkyl or nitro-substituted alkyl radical, an alkenyl, halogen-substituted alkenyl, alkinyl, halogen-substituted alkinyl, alkoxy-substituted alkyl radical, ammonium substituted by alkyl and hydroxy alkyl radicals;

$R_2$ and $R_3$ are selected from a group consisting of H and K;

Me is selected from a group consisting of K, alkaline earth metal cations, aluminum atom; ammonium cation; and n is a whole number from 1 to 3, equal to the valence of Me.

It will be appreciated that foliar applications of the inventive compositions will be effective as a common agricultural practice to control root pathogens caused by Phytophthoran, Phythium, and foliar infections caused by Plasmopara.

It will also be appreciated that the inventive compositions will have biocidal and arthropod pest control activity, and also have fertilizer effects, in plants. (See e.g., U.S. Pat. Nos. 5,206,228, 5,133,891 and 5,514,200).

The disclosures in all references cited herein are incorporated by reference.

What is claimed is:

1. A fungicidal composition for controlling fungus disease in plants comprising:
    enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution and each of said first and second salt being present in solution from about 20 millimole to about 5% vol./vol.

2. A fungicidal composition for controlling fungus disease in plants comprising:
    enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight.

3. A method of controlling fungus disease in plants comprising:
    applying to the plants in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution and each of said first and second salt being present in solution from about 20 millimole to about 5% vol./vol.

4. A method of controlling fungus disease in plants comprising:

applying to the plants in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight.

5. A fungicidal composition for controlling fungus disease in plants comprising:

enhanced fungicidally effective amounts of $KH_2PO_3$ and $K_2HPO_4$ wherein said composition comprises an aqueous solution and each said effective amounts of $KH_2PO_3$ and $K_2HPO_4$ being present in solution from about 20 millimole to about 5% vol./vol.

6. A fungicidal composition for controlling fungus disease in plants comprising:

enhanced fungicidally effective amounts of $KH_2PO_3$ and $K_2HPO_4$ wherein said effective amount of $KH_2PO_3$ is one part by weight and the said effective amount of $K_2HPO_4$ is between 0.001 and 1,000 parts by weight.

7. A method of controlling fungus disease in plants comprising: applying to the plants in enhanced fungicidally effective amounts of $KH_2PO_3$ and $K_2HPO_4$ salts, wherein said salts comprises an aqueous solution, wherein said effective amounts of $KH_2PO_3$ and $K_2HPO_4$ each being present in solution from about 20 millimole to about 5% vol./vol.

8. A method of controlling fungus disease in plants comprising: applying to the plants in enhanced fungicidally effective amounts of $KH_2PO_3$ and $K_2HPO_4$ salts, wherein said effective amount of $KH_2PO_3$ is one part by weight and the said effective amount of $K_2HPO_4$ is between 0.001 and 1,000 parts by weight.

* * * * *

US005736164C1

(12) EX PARTE REEXAMINATION CERTIFICATE (4859th)
United States Patent
Taylor

(10) Number: US 5,736,164 C1
(45) Certificate Issued: Oct. 7, 2003

(54) FUNGICIDAL COMPOSITIONS FOR PLANTS CONTAINING PHOSPHONATE AND PHOSPHATE SALTS, AND DERIVATIVES THEREOF

(75) Inventor: John B. Taylor, DeLan, FL (US)

(73) Assignee: Foliar Nutrients, Inc., Cairo, GA (US)

Reexamination Request:
No. 90/005,874, Dec. 6, 2000

Reexamination Certificate for:
Patent No.: 5,736,164
Issued: Apr. 7, 1998
Appl. No.: 08/705,594
Filed: Aug. 30, 1996

(51) Int. Cl.$^7$ .............................................. A01N 59/26
(52) U.S. Cl. ....................................... 424/601; 424/605
(58) Field of Search .................................. 424/606, 601

(56) References Cited

U.S. PATENT DOCUMENTS

| | | | |
|---|---|---|---|
| 1,935,599 A | 11/1933 | Rippey | 99/1 |
| 3,798,020 A | 3/1974 | Parham, Jr. et al. | 71/1 |
| 4,075,324 A | 2/1978 | Thizy et al. | 424/128 |
| 4,119,724 A | 10/1978 | Thizy et al. | 424/45 |
| 4,139,616 A | 2/1979 | Ducret et al. | 424/222 |
| 4,542,023 A | 9/1985 | Lacroix et al. | 514/126 |
| 4,698,334 A | 10/1987 | Horriere et al. | 424/143 |
| 4,755,614 A | 7/1988 | Corbet | 558/134 |
| 4,780,458 A | 10/1988 | Hodakowski et al. | 514/112 |
| 4,806,445 A | 2/1989 | Horriere et al. | 514/141 |
| 4,849,219 A | 7/1989 | Staub et al. | 514/144 |
| 4,935,410 A | 6/1990 | Barlet | 514/75 |
| 5,070,083 A | 12/1991 | Barlet | 514/144 |
| 5,124,344 A | 6/1992 | Greiner et al. | 514/383 |
| 5,133,891 A | 7/1992 | Barr et al. | 252/70 |
| 5,169,646 A | 12/1992 | Horriere et al. | 424/632 |
| 5,206,228 A | 4/1993 | Collins | 514/141 |
| 5,246,953 A | 9/1993 | Greiner et al. | 514/383 |
| 5,290,791 A | 3/1994 | Greiner et al. | 514/383 |
| 5,342,835 A | 8/1994 | Pepin et al. | 514/227.5 |
| 5,358,958 A | 10/1994 | Greiner et al. | 514/383 |
| 5,395,418 A | 3/1995 | Vetanovetz et al. | 71/29 |
| 5,514,200 A | 5/1996 | Lovatt | 71/11 |
| 5,707,414 A | 1/1998 | Hsu | 71/32 |
| 5,865,870 A | 2/1999 | Hsu | 71/32 |
| 6,168,643 B1 | 1/2001 | Hsu | 71/32 |

OTHER PUBLICATIONS

Patsy's Nursery Chemical Sprays, p. 5.*
Aliette WDG, Chemical Warning and Description Label, p. 2.*
8–8–8 Application For Registration of Commercial Fertilizer, p. 1.*
Nutrilan, Premium Foliar Feed Nutritional Label, p. 1.*
Reuveni, M.; Reuveni R.; Efficacy of Foliar Application of Phosphates in Controlling Powdery Mildew Fungus on Field–Grown Winegrapes: Effects on Cluster Yield and Peroxidase Activity in Berries; J. Phytopatholy, vol. 143(1), 21–25 (1995).

Affidavit with exhibit submitted by Dr. Carol J. Lovatt in prior patent infringement litigation between Rhone–Poulenc Agrochimie, S.A., and Biagro Western Sales, Inc., and filed with the court on Sep. 21, 1994.
Reuveni, M.; Agapov, V.; Reuveni, R.; Induction of Systemic Resistance to Powdery Mildew and Growth Increase in Cucumber by Phosphates; Biological Agriculture and Horticulture, 9: 305–315 (1993).
Reuveni, R.; Agapov, V.; Raviv, M.; Effects of Foliar Sprays of Phosphates on Powdery Mildew (*Sphaerotheca pannosa*) of Roses; J. Phytopathology, 142: 331–337 (1994).
Reuveni, M.; Agapov, V.; Reuveni, R.; Induced Systemic Protection to Powdery Mildew in Cucumber by Phosphate and Potassium Fertilizers: Effects of Inoculum Concentration and Post–Inoculation Treatment; Canadian J. Plant Pathol. 17: 247–251 (1994).
Reuveni, R.; Reuveni, M., Agapov, V.; Induction of Growth Increase and Systemic Resistance to *Exserobilum turcicum* in Maize by Foliar Spray of Phosphates; J. Phytopathology, 141: 337–346 (1994).
Reuveni, M.; Reuveni, R.; Efficacy of Foliar Sprays of Phosphates in Controlling Powdery Mildews in FieldGrown Nectarine, Mango Trees and Grapevines; Crop Protection, 14(4) 311–314 (1995).
Reuveni, M.; Agapov, V.; Reuveni, R.; Suppression of Cucumber Powdery Mildew (*Spaerotheca fuliginea*) by Foliar Sprays of Phosphate and Potassium Salts; Plant Pathology, 44: 31–39 (1995).
MacIntire, W.H.; Winterberg, S.H.; Hardin, L.J.; Sterges, A.J.; Clements, L.B.; Fertilizer Evaluation of Certain Phosphorus, Phosphorous, and Phosphoric Materials by Means of Pot Cultures; Agronomy Journal, vol. 42, pp. 543–549 (1950).
Fenn, M.E.; Coffey, M.D.; Studies of the In Vitro and In Vivo Antifungal Activity of Fosetyl–Al and Phosphorous Acid; Phytopathology, vol. 74, No. 5, pp. 606–611 (1984).
Griffith, Julia M.; Coffey, Michael D.; Grant, Bruce R.; Phosphonate inhibition as a function of phosphate concentration in isolates of *Phytophthora palmivora*; J. of General Microbiology, 139: 2109–2116 (1993).
Dolan, T.E.; Coffey, M.D.; Correlative in Vitro and in Vivo Behavior of Mutant Strains of *Phytophthora palmivora* Expressing Different Resistances to Phosporous Acid and Fosetyl–Na; Phytopathology, vol. 78, No. 7 (1988).
Technical specification sheets for Albrite® 70% Phosphorous Acid.
Technical bulletin for Albrite® 70% Phosphorous Acid.
Technical bulletin for Albrite® Phosphorous Acid Flake.
Abstract of Reuveni, M.; Zehavi T.; Reuveni R.; Integrated Control of Grape Powdery Mildew By Foliar Sprays of Potassium Phosphate; Phytoparasitica (24, No. 2, 153, 1996).

*Primary Examiner*—Alton Pryor

(57) ABSTRACT

A fungicidal composition for plants containing phosphonate and phosphate salts, and derivatives thereof is disclosed. The composition provides a single product which may be employed to control parasitic fungi in plants through mitigation of pathological acerbation of certain fungi.

OTHER PUBLICATIONS

Frazier, A.W. & Waerstad, K.R.; Crystallography And Equilibrium Solubility For Ammonium And Potassium Orthophosphites And Hypophosphites, Fertilizer Research 32, pp 161–168, May 19, 1992.

Effect of Phosphite on Tomato and Pepper Plants And On Susceptibility of Pepper to Phytophthora Root And Crown Rot In Hydroponic Culture; H. Forster, J.E. Adaskaveg, D.H. Kim, and M.E. Staghellini, The American Phytopathological Society, Plant Disease, vol. 82, No. 10, 1998, pp. 1165–1169.

Biagro Western Sales, Inc. brochure NutriPhite Fertilizers, P Foliar 4–30–8, Foliar Nutrient for Vegetable and Permanent Crops (1997); MSDS (Nov. 20, 1996); product label marked with Patent 5,514,200 which Owner previously cited.

Biagro Western Sales, Inc. brochure NutriGrow Fertilizers, PK 0–28–26, Foliar Nutrient for Nursery Crops, Turf and Commercial Landscapping (1997); MSDS (Sep. 26, 1997); product label marked with Patent 5,514,200 which Owner previously cited.

Biagro Western Sales, Inc. brochure NutriPhite Fertilizers, P Soil 0–40–0, Soil Nutrient for Vegitable and Permanent Crops (1997); MSDS (Sep. 26, 1997); product label.marked with Patent 5,514,200 which Owner previously cited.

Agrichem Manufacturing Industries Pty, Ltd. Brochure, Supa Crop, Supa Stand Phos, 1990.

The Effects of Sub–toxic Levels of Phosphonate on the Metabolism and Potential Virulence Factors of *Phytophthora Palmivora,* R.H. Dunstan, R.H. Smilie and B.R. Grant, Physiological and Molecular Plant Pathology (1990) 36, pp. 205–220.

The Use of Red Phosphorus as a Fertilizer, Part 3. Pot Trials with Perennial Ryegrass and White Clover; Widdowson, Soil Bureau, and H.P. Rothbaum, Chemistry Division, Department of Scientific and Industrial Research, Wellington; pp. 427–445.

Bacterial Oxidation of Orthophosphite; George Malacinski and Walter A. Konetzka, Department of Bacteriology, Indiana University, Bloomington, Indiana; pp. 578–582.

Transition of Phosphite to Phosphate in Soils; Fred Adams and John P. Conrad; pp. 361–371.

The Complex Mode of Action of Phosphonates, D.I. Guest and G. Bampeix, Australasian Plant Pathology, vol. 19, No. 4, 1990; pp. 113–115.

The Biological Inactivity of Glucose 6–Phosphite, Inorganic Phosphites and Other Phosphites, H.E. Robertson and P.D. Boyer, Archives of Biochemistry and Biophysics, The Merck Index, Dec. 9, 1995, $11^{th}$ Edition, 1989, pp. 380–381.

The Mechanism of Phosphonic (Phosphorouse) Acid in Phytophthora, B.R. Grant, R.H. Dunstan, J.M. Griffith, J.O. Niere, and R.H. Smillie, Australasian Plant Pathology, vol. 19, No. 4, 1990, pp. 115–121.

The Manufacture and Properties of Phosphonic (Phosphorus) Acid, R.H. Dunhill, Australasian Plant Pathology, vol. 19, No. 4, 1990; pp. 138–139.

Patsy's Nursery Chemical Sprays, 5 Pages.

Aliette WDG, Chemical Warning and Description Label, 2 Pages.

Application for Registration of Commercial Fertilizer, 1 Page.

Nutrilan, Premium Inorganic Foliar Feed Nutritional Label, 1 Page.

Aliette Technical Bulletin, Rhone–Poulenc AG Company, Feb. 22, 1989.

Comparative Antifungal Activity of Four Phosphonate Compounds Against Isolates of NIN Phytophthora Species, The American Phytopathological Society, vol. 79, No. 7, 1989, pp. 761–767.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2, 4, 6 and 8 is confirmed.

Claims 1, 3, 5 and 7 are determined to be patentable as amended.

1. A fungicidal composition for controlling fungus disease in plants comprising:
   enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution and each of said first and second salt being present in solution from about 20 [millimole] *millimolar* to about 5% vol./vol.

3. A method of controlling fungus disease in plants comprising:
   applying to the plants in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution and each of said first and second salt being present in solution from about 20 [millimole] *millimolar* to about 5% vol./vol.

5. A fungicidal composition for controlling fungus disease in plants comprising:
   enhanced fungicidally effective amounts of $KH_2PO_3$ and $K_2HPO_4$ wherein said composition comprises an aqueous solution and each said effective amounts of $KH_2PO_3$ and $K_2HPO_4$ being present in solution from about 20 [millimole] *millimolar* to about 5% vol./vol.

7. A method of controlling fungus disease in plants comprising: applying to the plants in enhanced fungicidally effective amounts of $KH_2PO_3$ and $K_2HPO_4$ salts, wherein said salts comprises an aqueous solution, wherein said effective amounts of $KH_2PO_3$ and $K_2HPO_4$ each being present in solution from about 20 [millimole] *millimolar* to about 5% vol./vol.

* * * * *

(12) EX PARTE REEXAMINATION CERTIFICATE (6185th)

United States Patent
Taylor

(10) Number: US 5,736,164 C2
(45) Certificate Issued: Apr. 8, 2008

(54) FUNGICIDAL COMPOSITIONS FOR PLANTS CONTAINING PHOSPHONATE AND PHOSPHATE SALTS, AND DERIVATIVES THEREOF

(75) Inventor: John B. Taylor, DeLan, FL (US)

(73) Assignee: Foliar Nutrients, Inc., Cairo, GA (US)

Reexamination Request:
No. 90/007,228, Oct. 1, 2004

Reexamination Certificate for:
Patent No.: 5,736,164
Issued: Apr. 7, 1998
Appl. No.: 08/705,594
Filed: Aug. 30, 1996

Reexamination Certificate C1 5,736,164 issued Oct. 7, 2003

(51) Int. Cl.
*A01N 59/26* (2006.01)

(52) U.S. Cl. ........................... 424/601; 424/605
(58) Field of Classification Search ............ 424/601, 424/605, 772; 504/101
See application file for complete search history.

(56) References Cited

U.S. PATENT DOCUMENTS

| 4,075,324 | A | * | 2/1978 | Thizy et al. | 424/601 |
| 4,334,910 | A | * | 6/1982 | Lorincz et al. | 504/124 |
| 4,350,770 | A | * | 9/1982 | Spraker | 435/252.4 |
| 6,284,286 | B1 | * | 9/2001 | Arimoto et al. | 424/682 |

OTHER PUBLICATIONS

Dolan and Coffey, Phytopathology (1988), vol. 78, No. 7, pp. 974–978.*
Fenn and Coffey, Phytopathology (1984), vol. 74, No. 5, pp. 606–611.*
Reuveni et al., "Induction of growth increase and systemic resistance to *Exserohilum turcicum* in maize by foliar spray of phosphates", J. Phytopathology (1994), vol. 141, pp. 337–346.*
Reuveni et al., "Suppression of cucumber powdery mildew (*Sphaerotheca fuliginea*) by foliar sprays phosphate and potassium salts", Plant Pathology (1995), vol. 44, pp. 31–39.*
Dunstan et al., "The effects of sub–toxic levels of phosphonate on the metabolism and potential virulence factors of *Phytophtho palmivora*", Physiological and Molecular Plant Pathology (1990), vol. 36, pp. 205–220.*
Fenn, "Evidence for the direct mode of action of fosetyl–aluminum and phosphorous acid", University Microfilms International (1986), No. 8623035, pp. i–xii, 1–103.*
Walker, "Effects of phosphite and phosphate concentrations in agar on mycelial growth of fungi", Fungic. Nematic. Tests (1994), vol. 49, p. 381.*
Fluid Fertilizer Manual (1985), pp. 5–4—5–7, 6–1—6–22.*

* cited by examiner

*Primary Examiner*—Gary L. Kunz

(57) ABSTRACT

A fungicidal composition for plants containing phosphonate and phosphate salts, and derivatives thereof is disclosed. The composition provides a single product which may be employed to control parasitic fungi in plants through mitigation of pathological acerbation of certain fungi.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, line 4:

*Under certain pH, phosphite may precipitate out of the solution which renders the phosphite unavailable for plant uptake. Therefore, the aqueous solution of the present disclosure should have a pH that is suitable for plant uptake while doing no harm to the plant. The term "a pH that is acceptable for phosphorus uptake in plant foliage" refers to the pH that allows phosphorous to be efficiently absorbed by the plant without causing damage to the foliage. The pH that is acceptable for phosphorus uptake in plant foliage usually ranges between about 5.0 to about 7.0, and preferably between about 5.5 to about 6.5. Phosphorus is most readily taken up by foliage at a pH value of about 6.0. Depending on the plant species, a pH below 5.0 may cause damage to leaves and/or the flowers and/or fruit. Although a pH between about 7.0 to about 7.5 generally causes no plant damage, there may be reduced uptake of nutrients at that pH range. Depending on the plant species, a pH between about 7.5 and 8.0 may result in plant damage. A pH greater than 8.0, generally causes damage to the plant in addition to reducing uptake of the phosphorous by the plant foliage.*

AS A RESULT OF REEXAMINATION, IT HAS BEEN DETERMINED THAT:

The patentability of claims 3–4 and 7–8 is confirmed.

Claims 1–2 and 5–6 are cancelled.

New claims 9–28 are added and determined to be patentable.

9. *A fungicidal composition for controlling fungus disease in plants comprising:*

*enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution having a pH ranging from 5.0 to 7.0, each of said first and second salt being present in solution from about 20 millimolar to about 5% vol./vol.*

10. *A fungicidal composition for controlling fungus disease in plants comprising:*

*enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight, and said fungicidal composition having a pH ranging from 5.0 to 7.0.*

11. *A method of controlling fungus disease in plants comprising:*

*applying to the plants a composition in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution having a pH ranging from 5.0 to 7.0, each of said first and second salt being present in solution from about 20 millimolar to about 5% vol./vol.*

12. *A method of controlling fungus disease in plants comprising:*

*applying to the plants a composition in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight, and said composition having a pH ranging from 5.0 to 7.0.*

13. *A fungicidal composition for controlling fungus disease in plants comprising:*

*enhanced fungicidally effective amounts of $KH_2PO_3$ and $K_2HPO_4$ wherein said composition comprises an aqueous solution and each said effective amounts of $KH_2PO_3$ and $K_2HPO_4$ being present in solution from about 20 millimolar to about 5% vol./vol. and said fungicidal composition having a pH ranging from 5.0 to 7.0.*

14. *A fungicidal composition for controlling fungus disease in plants comprising:*

*enhanced fungicidally effective amounts of $KH_2PO_3$ and $K_2HPO_4$ wherein said effective amount of $KH_2PO_3$ is one part by weight and the said effective amount of $K_2HPO_4$ is between 0.001 and 1,000 parts by weight, and said fungicidal composition having a pH ranging from 5.0 to 7.0.*

15. *A method of controlling fungus disease in plants comprising:*

*applying to the plants in enhanced fungicidally effective amounts of $KH_2PO_3$ and $K_2HPO_4$ salts, wherein said salts comprises an aqueous solution having a pH ranging from 5.0 to 7.0, wherein said effective amounts of $KH_2PO_3$ and $K_2HPO_4$ each being present in solution from about 20 millimolar to about 5% vol./vol.*

16. *A method of controlling fungus disease in plants comprising:*

*applying to the plants a composition in enhanced fungicidally effective amounts of $KH_2PO_3$ and $K_2HPO_4$ salts, wherein said effective amount of $KH_2PO_3$ is one part by weight and the said effective amount of $K_2HPO_4$ is between 0.001 and 1,000 parts by weight, and said composition having a pH ranging from 5.0 to 7.0.*

17. *A method of controlling fungus disease in plants consisting essentially of:*

*applying to the plants in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution and each of said first and second salt being present in solution from about 20 millimolar to about 5% vol./vol.*

18. A method of controlling fungus disease in plants consisting essentially of:

applying to the plants in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight, $KH_2PO_3$ and $K_2HPO_4$ salts, wherein said effective amount of $KH_2PO_3$ is one part by weight and the said effective amount of $K_2HPO_4$ is between 0.001 and 1,000 parts by weight, and said composition having a pH ranging from 5.0 to 7.0.

19. A method of controlling fungus disease in plants consisting essentially of:

applying to the plants in enhanced fungicidally effective amounts of $KH_2PO_3$ and $K_2HPO_4$ salts, wherein said salts comprises an aqueous solution, wherein said effective amounts of $KH_2PO_3$ and $K_2HPO_4$ each being present in solution from about 20 millimolar to about 5% vol./vol.

20. A method of controlling fungus disease in plants consisting essentially of:

applying to the plants in enhanced fungicidally effective amounts of $KH_2PO_3$ and $K_2HPO_4$ salts, wherein said effective amount of $KH_2PO_3$ is one part by weight and the said effective amount of $K_2HPO_4$ is between 0.001 and 1,000 parts by weight.

21. A fungicidal composition for controlling fungus disease in plants consisting essentially of:

enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution having a pH ranging from 5.0 to 7.0, each of said first and second salt being present in solution from about 20 millimolar to about 5% vol./vol.

22. A fungicidal composition for controlling fungus disease in plants consisting essentially of:

enhanced fungicidally effective amounts of at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight, and said fungicidal composition having a pH ranging from 5.0 to 7.0.

23. A method of controlling fungus disease in plants consisting essentially of:

applying to the plants a composition in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein said composition comprises an aqueous solution having a pH ranging from 5.0 to 7.0, each of said first and second salt being present in solution from about 20 millimolar to about 5% vol./vol.

24. A method of controlling fungus disease in plants consisting essentially of:

applying to the plants a composition in enhanced fungicidally effective amounts at least a first salt selected from a group consisting of $K_2HPO_3$, $KH_2PO_3$ and $K_3PO_3$; and a second salt selected from a group consisting of $K_2HPO_4$, $KH_2PO_4$ and $K_3PO_4$ wherein the amount of said first said salt is one part by weight and the amount of said second salt is between 0.001 and 1,000 parts by weight, and said composition having a pH ranging from 5.0 to 7.0.

25. A fungicidal composition for controlling fungus disease in plants consisting essentially of:

enhanced fungicidally effective amounts of $KH_2PO_3$ and $K_2HPO_4$ wherein said composition comprises an aqueous solution and each said effective amounts of $KH_2PO_3$ and $K_2HPO_4$ being present in solution from about 20 millimolar to about 5% vol./vol. and said fungicidal composition having a pH ranging from 5.0 to 7.0.

26. A fungicidal composition for controlling fungus disease in plants consisting essentially of:

enhanced fungicidally effective amounts of $KH_2PO_3$ and $K_2HPO_4$ wherein said effective amount of $KH_2PO_3$ is one part by weight and the said effective amount of $K_2HPO_4$ is between 0.001 and 1,000 parts by weight, and said fungicidal composition having a pH ranging from 5.0 to 7.0.

27. A method of controlling fungus disease in plants consisting essentially of:

applying to the plants in enhanced fungicidally effective amounts of $KH_2PO_3$ and $K_2HPO_4$ salts, wherein said salts comprises an aqueous solution having a pH ranging from 5.0 to 7.0, wherein said effective amounts of $KH_2PO_3$ and $K_2HPO_4$ each being present in solution from about 20 millimolar to about 5% vol./vol.

28. A method of controlling fungus disease in plants consisting essentially of:

applying to the plants a composition in enhanced fungicidally effective amounts of $KH_2PO_3$ and $K_2HPO_4$ salts, wherein said effective amount of $KH_2PO_3$ is one part by weight and the said effective amount of $K_2HPO_4$ is between 0.001 and 1,000 parts by weight, and said composition having a pH ranging from 5.0 to 7.0.

* * * * *